United States Patent [19]
Edgar et al.

[11] Patent Number: 5,848,395
[45] Date of Patent: Dec. 8, 1998

[54] APPOINTMENT BOOKING AND SCHEDULING SYSTEM

[76] Inventors: James William Hardie Edgar, 86 Beechwood Grove, Uphall Station, West Lothian EH54 5QJ, Scotland; Peter John Gathercole, 47 Hillcrest Rise, Cookridge, Leeds LS16 7DJ, England; Michael Alan Johnson, 4 Highlands lane, Chalfont St Peter, Gerrards Cross SL9 0DL, England; Alistair Edward Roycroft, Flat 1, 10 Rathen Road, Withington, Manchester M20 4GH, England; Alan Smith, 34 Lakelands Drive, Ladybridge, Bolton Bl3 4NN, England; Donald Brian Webster, 48 Lakeside, Bracknell, Berks RG42 2LE, England

[21] Appl. No.: 673,728

[22] Filed: Jun. 26, 1996

[30] Foreign Application Priority Data

Mar. 23, 1996 [GB] United Kingdom .................... 9606194

[51] Int. Cl.⁶ .................................................. G06F 17/60
[52] U.S. Cl. ...................................................... 705/9; 705/5
[58] Field of Search .................................... 705/5, 9, 1, 8; 364/468.06, 468.08, 468.05, 472.05, 478.11, 479.02

[56] References Cited

U.S. PATENT DOCUMENTS

| | | | |
|---|---|---|---|
| 4,769,796 | 9/1988 | Levine | 368/29 |
| 4,780,800 | 10/1988 | Levine | 379/67 |
| 4,852,001 | 7/1989 | Tsushima et al. | 705/8 |
| 5,272,638 | 12/1993 | Martin et al. | 701/202 |
| 5,442,730 | 8/1995 | Bigus | 395/22 |
| 5,525,958 | 6/1996 | Negishi et al. | 340/309.15 |
| 5,541,845 | 7/1996 | Klein | 701/207 |
| 5,615,121 | 3/1997 | Babayev et al. | 705/9 |
| 5,666,493 | 9/1997 | Wojcik et al. | 705/26 |
| 5,737,728 | 4/1998 | Sisley et al. | 705/8 |

FOREIGN PATENT DOCUMENTS

| | | | |
|---|---|---|---|
| 0 669 586 | 8/1995 | European Pat. Off. | G06F 17/60 |
| 0 672 990 | 9/1995 | European Pat. Off. | G06F 17/60 |
| WO 95/26535 | 10/1995 | European Pat. Off. | |
| WO 95/26535 | 10/1995 | WIPO . | |

OTHER PUBLICATIONS

Edgar, et al., "Computerized booking and scheduling system . . .", INT Computers Ltd, Dialog file 351, Accession No. 011538556, Aug. 4, 1997.

Collins, "Automated Assignment and Scheduling of Service Personnel", IEEE Expert, vol. 9, No. 2, Apr. 1994, pp. 33–39.

Azarmi, "Workforce scheduling with constraint logic programming", BT Technology Journal, vol. 13, No. 1, Jan., 1995, pp. 81–94.

Laithwaite, "Work allocation challenges and solutions in a large–scale work management environment", BT Technology Journal, vol. 13, No. 1, Jan., 1995, pp. 46–54.

*Primary Examiner*—Allen R. MacDonald
*Assistant Examiner*—Romain Jeanty
*Attorney, Agent, or Firm*—Lee, Mann, Smith, McWilliams, Sweeney & Ohlson

[57] ABSTRACT

An appointment booking and scheduling system is described, for booking appointments with operatives (e.g. service engineers) visiting customer sites within a defined geographic area. The system includes a table for storing a number of routes, each of which specifies a sequence of regions to be visited by a particular operative, and jobs to be performed by the operative in each of the regions. An appointment server is provided for offering appointments at specified times, using the table to check for availability of operatives in specified regions at specified times, and for inserting new jobs in the routes to reflect booked appointments. A scheduler periodically updates the routes e.g by means of a simulated annealing process, to generate a new set of routes.

4 Claims, 3 Drawing Sheets

APPOINTMENT BOOKING AND SCHEDULING SYSTEM

BACKGROUND TO THE INVENTION

This invention relates to an appointment booking and scheduling system. The invention is particularly, although not exclusively, concerned with a system for booking appointments with service engineers visiting customer sites within a defined geographic area.

The object of the invention is to provide an improved appointment booking and scheduling system.

SUMMARY OF THE INVENTION

According to the invention there is provided an appointment booking and scheduling system comprising:

(a) a table for storing a plurality of routes, each of which specifies a sequence of regions to be visited by a particular operative, and jobs to be performed by the operative in each of the regions;

(b) an appointment server for offering appointments at specified times, using the table to check for availability of operatives in specified regions at specified times, and for inserting new jobs in the routes to reflect booked appointments; and (c) a scheduler for periodically updating the routes in accordance with predetermined scheduling criteria, to generate a new set of routes.

DESCRIPTION OF AN EMBODIMENT OF THE INVENTION

One appointment booking and scheduling system in accordance with the invention will now be described by way of example with reference to the accompanying drawings. The system to be described is intended to handle appointments for a number of operatives (e.g. service engineers), visiting customer sites within a defined geographic area.

Overview of the system

Figure 1:
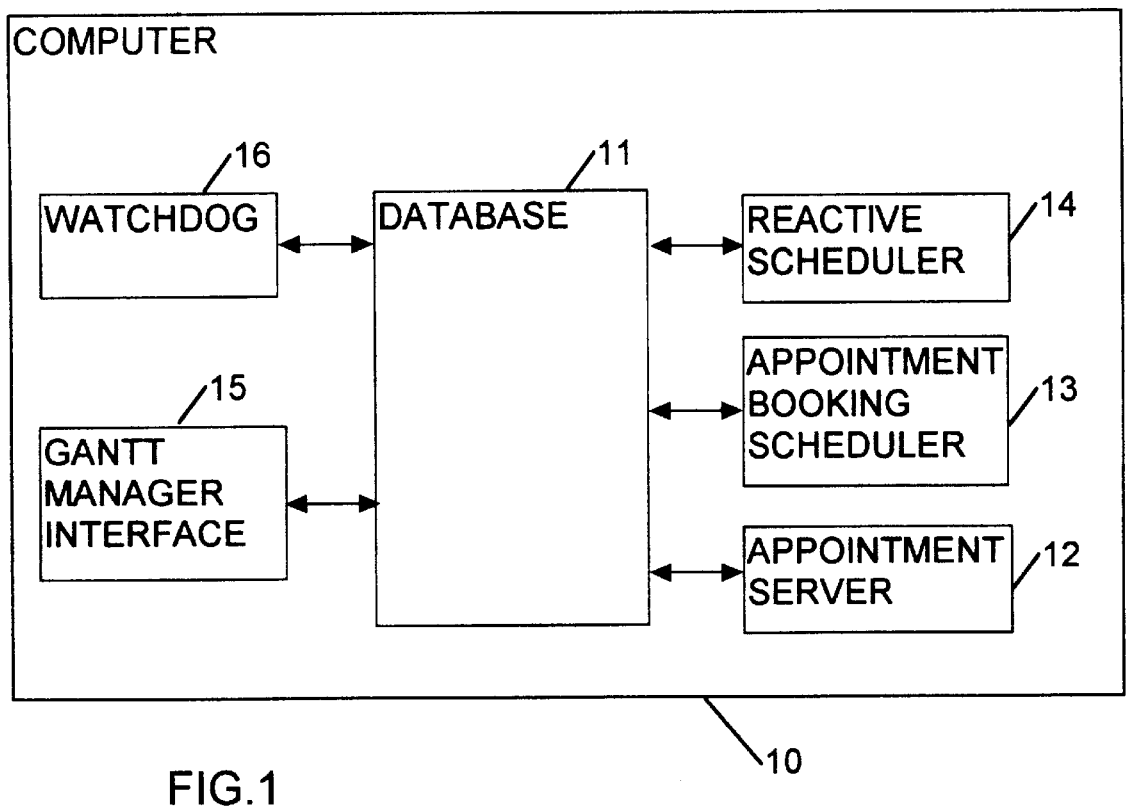
FIG. 1 is a block diagram of an appointment booking and scheduling system in accordance with the invention.

Referring to FIG. 1, the appointment booking and scheduling system comprises conventional computer hardware 10, having a processor, memory, display, input device, and disks (not shown). The computer hardware stores a database 11, and runs the following software: an appointment server 12, an appointment booking scheduler 13, a reactive scheduler 14, a Gantt manager interface 15, and a watchdog 16.

Figure 2:
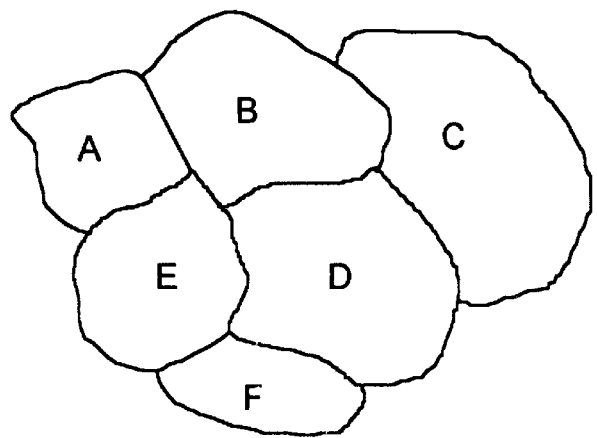
FIG. 2 is a schematic representation of a geographic area within which appointments are to be booked.

Referring to FIG. 2, the area in which appointments are to be booked is divided into a number of regions, designated A, B, C . . . Each of these regions includes a number of customer sites, the location of each of which may, for example, be indicated by its postal code.

Figure 3:
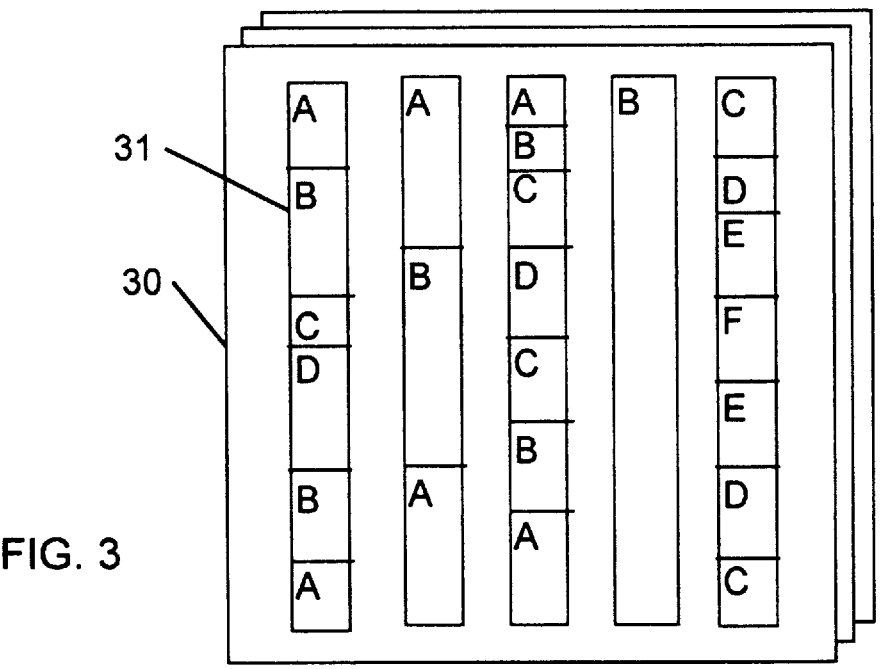
FIG. 3 is a schematic representation of a database holding a number of routes.

Referring to FIG. 3, the database 10 includes a number of tables 30, one for each day in a predetermined window in which appointments may be offered. For example, this window may cover two weeks from the current date. Each of the tables 10 contains a number of routes 31. Each route represents an itinerary for a particular operative on the day in question, and has a number of jobs associated with it. Each route comprises a sequence of records, with each record containing the following fields:

Region: the identity of a region to be visited by the operative.

Start Time: the time the operative is scheduled to start working in the region.

End Time: the time the operative is scheduled to finish working in the region.

Time Used: the number of minutes scheduled to be spent on jobs already booked within the region.

Time Left: the number of minutes free, available for new jobs in the region.

The sum of Time Used and Time Left will normally equal the difference between Start Time and End Time.

Appointment server

Figure 4:
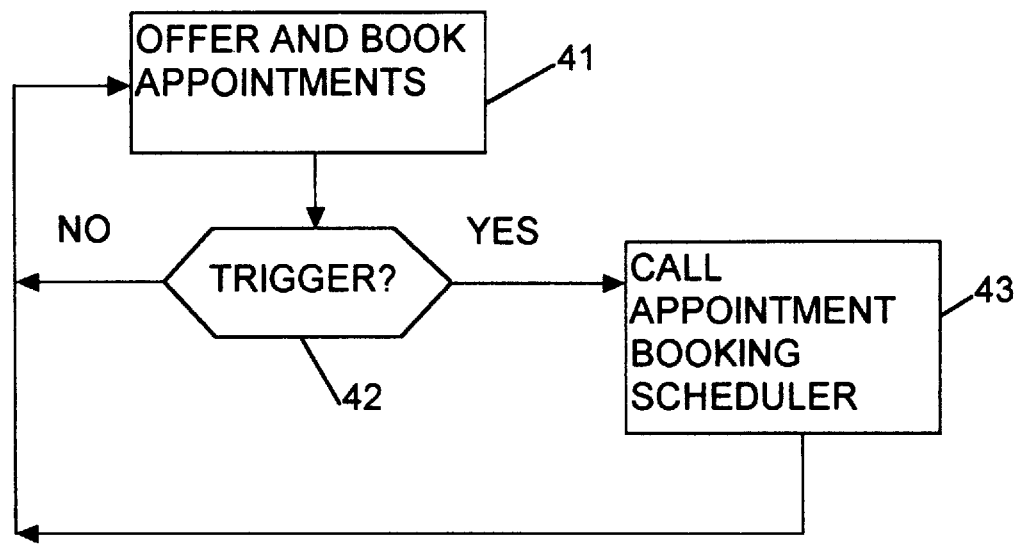
FIG. 4 is a flow chart showing the operation of an appointment server.

FIG. 4 shows the operation of the appointment server 12.

(Box 41) The appointment server uses the routes stored in the database to offer a number of possible appointments to customers. Specifically, if a customer within a particular region requests an appointment, the appointment server searches the routes to find one which visits the region and which contains sufficient free time within that region. Appointments are offered within predetermined time slots, e.g. two hour slots. If the customer accepts the offered appointment, a new job is associated with the route and the Time Used and Time Left fields are updated.

(Box 42) When an appointment is made, the appointment server checks whether a predetermined trigger number of appointments has been made since the last time the scheduler was run. If not, the appointment server returns to Box 41 to await the next appointment.

(Box 43) When the trigger number of appointments has been made, the appointment server calls the scheduler, and immediately returns to Box 41 to await the next appointment.

Appointment booking scheduler

When the appointment booking scheduler is called, it performs the following operations.

The scheduler first extracts the jobs to be scheduled. Appointment bookings and other tasks such as pre-allocated work and holiday activities are read in by the scheduler from the database. This includes any unavailability periods that may have been input through the Gantt or database maintenance screens.

The scheduler then takes the set of jobs to be scheduled, and allocates jobs to resources for specific times, accounting for travel times, to create a number of sequences of jobs. The scheduler then attempts to optimise each sequence, driven by weightings on a variety of parameters. The optimisation process is described in detail below with reference to FIG. 5.

The scheduler then uses the optimised sequences of jobs output from the optimisation process to create a new table 30 representing a new set of routes. First, it examines all the engineer shifts and subtracts time for booked jobs, to determine the total amount of free time. This time is allocated to the routes in such a way that each region receives the same proportion of time. As a result, each route has a sequence of available time slots associated with it.

Figure 5:
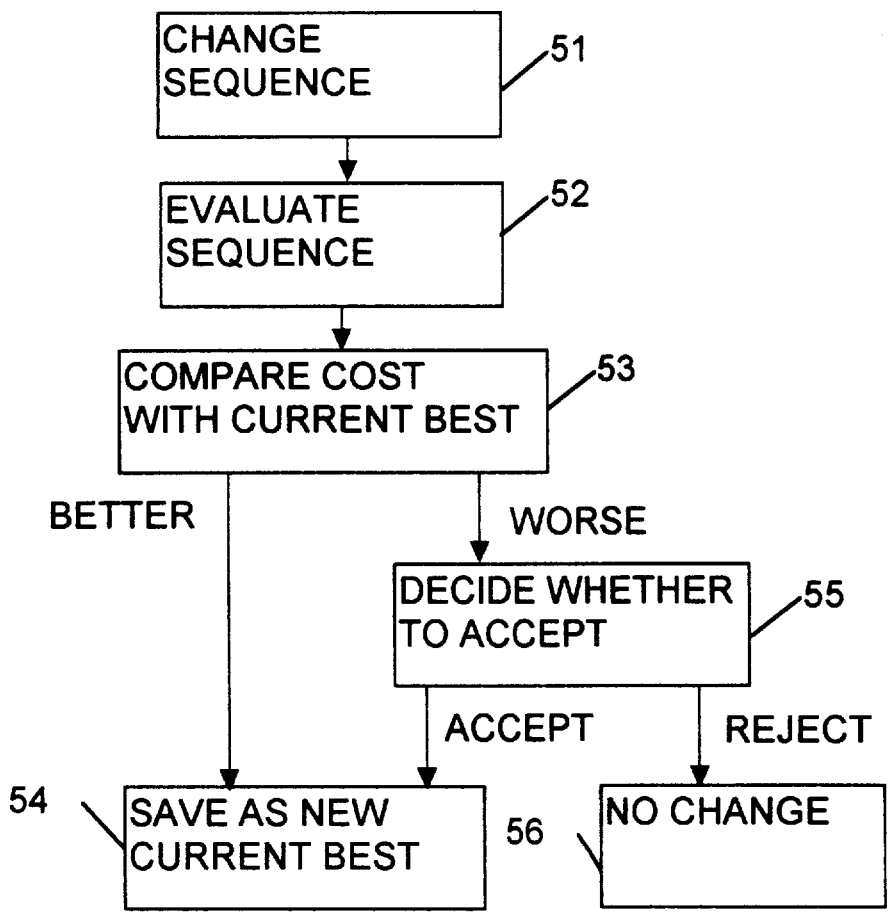
FIG. 5 is a flow chart showing an optimisation process performed by the an appointment booking scheduler.

The appointment booking scheduler 13 uses a simulated annealing process to attempt to optimise the scheduling of jobs within each sequence. This employs a simulated "temperature" which is initially set a high value, and gradually reduced until it reaches a predetermined final value. At each value of the simulated temperature, the process shown in FIG. 5 is performed a predetermined number of times N. The value of N can be varied according to the degree of optimisation desired: a high value of N gives better optimisation, but means that the scheduler takes longer to run.

At each iteration of this process, the scheduler stores a "current best" sequence of jobs, along with a corresponding "current best" cost value for that sequence. Referring to FIG. 5, each iteration of the process consists of the following steps.

(Box 51) The sequence of jobs is changed in some random way, e.g. by changing the order of two adjacent jobs in the sequence.

(Box 52) The changed sequence is then evaluated to determine a cost function for the route. This cost function may include factors such as time taken to travel between jobs, penalties for breaking an appointment, overtime working for operatives, and achieving a suitable match between the operatives' skills and the difficulty of the jobs.

(Box 53) The evaluated cost is then compared with the stored current best value.

(Box 54) If the evaluated cost is better (i.e. less) than the current best, the changed sequence is saved as the new current best sequence, and its cost is saved as the new current best cost.

(Box 55) If on the other hand the evaluated cost is greater than or equal to the current best value, the scheduler makes a random choice as to whether or not to accept this new sequence, with a probability determined by the current simulated temperature: the higher the simulated temperature, the more likely the scheduler is to accept the new sequence. If the scheduler decides to accept the new sequence, the changed sequence is saved as the new current best sequence, and its cost is saved as the new current best cost.

(Box 56) If on the other hand the new sequence is not accepted, the existing current best is retained.

Reactive scheduler

The reactive scheduler 14 is similar to the appointment booking scheduler, the main difference being that it is capable of optimising from the latest best position. The reactive scheduler takes over from the appointment booking scheduler when a predetermined horizon is crossed (e.g. on the day that the appointments are due), and takes account of last minute variations in resource availability and appointment cancellations, by rescheduling dynamically.

Gantt manager

The Gantt manager interface 15 allows the current routes to be viewed graphically in bar chart form, to provide an overview of the operation of the schedulers.

Watchdog

The watchdog 16 continuously monitors the status of all jobs and can initiate the appointment booking scheduler automatically if the number of appointments booked on a particular route exceeds a predetermined threshold level.

The watchdog also monitors the status of all jobs within the reactive scheduler horizon, and provides a warning of jeopardy situations.

Some possible modifications

It will be appreciated that many modifications may be made to the system described above without departing from the scope of the present invention. For example, instead of using a separate appointment booking scheduler and reactive scheduler, both functions may be performed by the same unit operating in different modes.

We claim:

1. A computerized appointment booking and scheduling apparatus for scheduling a plurality of operatives traveling to sites in a geographical area, said geographical area being divided into a plurality of regions, each of which regions includes a plurality of said sites, said apparatus comprising:

(a) a database for storing information relating to a plurality of appointments that have been booked, and for storing a plurality of routes, each of said routes comprising information specifying a sequence of said regions to be visited by a particular operative, the times the operative is scheduled to enter and leave each of said sequence of regions, and the amount of free time available for new appointments in each of said sequence of regions;

(b) an appointment server for offering appointments at specified times, using said routes stored in the database to check for availability of operatives in specified regions at specified times, and for inserting new appointments in the database and updating said routes to reflect said new appointments; and (c) an appointment scheduler for periodically accessing the database to obtain said information relating to appointments that have been booked, using this information to generate a new plurality of routes, optimizing said new plurality of routes in accordance with predetermined criteria, and writing said new plurality of routes into said database to replace the existing plurality of routes stored in said database.

2. Apparatus according to claim 1 further including means for checking whether a predetermined trigger number of appointments has been made since the last time said appointment scheduler was run and for running said appointment scheduler whenever said predetermined trigger number of appointments has been made.

3. A method of operating a computer apparatus to schedule a plurality of operatives traveling to sites in a geographical area, said geographical area being divided into a plurality of regions, each of which regions includes a plurality of said sites, said method comprising the steps:

(a) storing in a database information relating to a plurality of appointments that have been booked, and a plurality of routes, each of said routes comprising information specifying a sequence of said regions to be visited by a particular operative, the times the operative is scheduled to enter and leave each of said sequence of regions, and the amount of free time available for new appointments in each of said sequence of regions;

(b) offering appointments at specified times, using said routes stored in the database to check for availability of operatives in specified regions at specified times;

(c) booking new appointments, inserting the new appointments in the database, and updating said routes to reflect the new appointments; and (d) periodically accessing the database to obtain said information relating to appointments that have been booked, using this information to generate a new plurality of routes, optimizing said new plurality of routes in accordance with predetermined criteria, and writing said new plurality of routes into said database to replace the existing plurality of routes stored in said database.

4. A method according to claim 3 including the further step of checking whether a predetermined trigger number of appointments has been made since the last time said appointment scheduler was run, and running said appointment scheduler whenever said predetermined trigger number of appointments has been made.

* * * * *